(12) United States Patent
Mangold

(10) Patent No.: US 7,378,567 B2
(45) Date of Patent: May 27, 2008

(54) ABSORBENT BODY FOR HYGIENE ARTICLES

(75) Inventor: Rainer Mangold, Herbrechtingen (DE)

(73) Assignee: Paul Hartmann AG, Heidenheim (DE)

(*) Notice: Subject to any disclaimer, the term of this patent is extended or adjusted under 35 U.S.C. 154(b) by 341 days.

(21) Appl. No.: 10/488,626

(22) PCT Filed: Jul. 25, 2002

(86) PCT No.: PCT/EP02/08284

§ 371 (c)(1),
(2), (4) Date: Mar. 31, 2004

(87) PCT Pub. No.: WO03/022194

PCT Pub. Date: Mar. 20, 2003

(65) Prior Publication Data

US 2004/0254552 A1    Dec. 16, 2004

(30) Foreign Application Priority Data

Sep. 8, 2001    (DE) .............. 101 44 128

(51) Int. Cl.
- *A61F 13/15* (2006.01)
- *A61F 13/20* (2006.01)
- *B32B 27/14* (2006.01)
- *B29C 65/00* (2006.01)
- *B31F 1/07* (2006.01)

(52) U.S. Cl. ............ 604/380; 604/367; 604/378; 428/198; 156/196; 156/209

(58) Field of Classification Search ............... 604/365, 604/375, 373, 378, 368, 374; 428/171, 196, 428/198, 286, 287
See application file for complete search history.

(56) References Cited

U.S. PATENT DOCUMENTS

| | | | | | |
|---|---|---|---|---|---|
| 3,721,242 | A | * | 3/1973 | Krusko | 604/365 |
| 4,041,951 | A | * | 8/1977 | Sanford | 604/375 |
| 4,065,402 | A | * | 12/1977 | Satterwhite et al. | 516/126 |
| 4,559,050 | A | * | 12/1985 | Iskra | 604/368 |
| 4,590,114 | A | | 5/1986 | Holtman | |
| 4,605,402 | A | * | 8/1986 | Iskra | 604/368 |
| 4,781,710 | A | | 11/1988 | Megison et al. | |
| 4,992,324 | A | * | 2/1991 | Dube | 442/118 |

(Continued)

FOREIGN PATENT DOCUMENTS

CA    2237154    4/1998

(Continued)

*Primary Examiner*—Melanie J. Hand
(74) *Attorney, Agent, or Firm*—Young Basile

(57) ABSTRACT

An absorbent body for hygiene articles, particularly sanitary napkins or panty liners, includes a liquid absorbing and distributing layer facing the body and made of a first fibrous material with a first pore size, and a liquid storage layer facing away from the body and including at least 20 to 98 wt. % cellulose fibers, with a second pore size smaller than the first pore size. The first fibrous material is made of interlinked cellulose fibers, and the layers are interconnected, without adhesives by a multitude of embossing points provided in grid-like manner which results in the formation of a funnel-shaped pore gradient in the liquid absorbing and distributing layer around the embossing points. This pore gradient assists in the introduction of liquid into the underlying storage layer.

10 Claims, 1 Drawing Sheet

U.S. PATENT DOCUMENTS

| | | | |
|---|---|---|---|
| 5,009,650 A | * 4/1991 | Bernardin | 604/378 |
| 5,176,668 A | * 1/1993 | Bernardin | 604/368 |
| 5,352,480 A | * 10/1994 | Hansen et al. | 427/202 |
| 5,360,420 A | * 11/1994 | Cook et al. | 604/378 |
| 5,447,977 A | * 9/1995 | Hansen et al. | 524/13 |
| 5,986,167 A | * 11/1999 | Arteman et al. | 604/380 |
| 6,355,200 B1 | 3/2002 | Schmidt et al. | |
| 6,428,799 B1 | * 8/2002 | Cen et al. | 424/402 |
| 6,443,936 B1 | * 9/2002 | Hamilton et al. | 604/387 |
| 6,626,880 B2 | * 9/2003 | Onishi | 604/385.101 |

FOREIGN PATENT DOCUMENTS

CA        2237154        * 9/1998

* cited by examiner

ABSORBENT BODY FOR HYGIENE ARTICLES

BACKGROUND

The invention relates to an at least double-layer absorbent body for hygiene articles, specifically for sanitary napkins or panty liners, having a fluid absorption and distribution layer facing the body made of a first fibrous material with a first pore size and a fluid storage layer facing away from the body with a second pore size.

An absorbent body structure of this type is known from a plurality of publications, for example, EP 0 512 010 B1. In the case of this known absorbent body, the fluid absorption and distribution layer facing the body is formed from intra-linked cellulose fibers, known as curled-fiber material, which, even in its saturated state, retains a high pore volume and therefore promotes the rapid uptake of large quantities of fluid without capillary interstices becoming blocked and causing the impinging fluid to run off to the sides. In this curled-fiber material, the fibers are stiffened by hydrogen-bridge bonds formed inside a cellulose fiber, and the fibrous material tends, with suitable pre-compression, to expand in a saturated state, i.e., to increase in volume. Other fibrous materials which are suitable for the fluid absorption and distribution layer facing away from the body are thermally welded thermoplastic bi-component fibers which, as a result of the thermal welding, do not tend to collapse when impinged upon by fluid.

The task of the fluid absorption and distribution layer facing the body is to absorb impinging fluid, to hold it temporarily and distribute it within the layer, and then to release it to a storage layer lying thereunder which has a smaller pore size and thus higher capillarity. The greater the pore size of a fibrous layer, the less its capacity to transport fluid within the layer on the basis of capillary mechanisms, i.e., the lower the capillarity of this layer and vice-versa. Because of the small capillary fiber interstices in the storage layer, the fluid is transported to still unused areas of the absorbent body as the result of capillary fluid transportation within the storage layer. This transportation process requires a certain time, for which reason rapidly absorbing fluid absorption and distribution layers of the previously described type are used.

The layers used here are intended to be bonded to each other in a suitable way to simplify the handling of large panels of web material, but also to prevent slippage of the layers against each other when a hygiene article is used. To this end, a plurality of methods and means are known, as for example, the use of pressure-sensitive adhesives, thermal bonding of fibrous webs with the addition of thermoplastic fiber materials or of adhesive materials or the application of weld joints. Further, the bonding of large panels of web material by calendaring is known at least in principle as a measure to the person skilled in the art, although a possibly unintentional compression of the web material may result.

From EP 1 032 342 B1 it is known for example, for the adhesive-free production of a fibrous material web consisting of cellulose fibers, starting with an air-laid cellulose fibrous nonwoven, to take this nonwoven through the gap of a pair of calendaring rollers, where the pair of calendaring rollers has punctiform elevations which can be positioned opposite each other to almost touch and produce embossing points on both sides in the nonwoven and thus bond the nonwoven.

SUMMARY

The object of the present invention is to achieve a satisfactory bond between the layers in a double-layer absorbent body of the type initially described, where the difference in pore sizes in the absorption and distribution layer facing the body and in the storage layer facing away from the body is to be retained to the greatest degree possible, so that the absorbent body achieves good fluid absorption, distribution and storage properties.

This object is achieved by an absorbent body where the first fibrous material of the fluid absorption and distribution layer facing the body consists of air-laid intralinked cellulose fibers and where the layers are bonded without adhesive by a plurality of embossing points arranged in a grid, and whereby a funnel-shaped pore gradient is formed in the fluid absorption and distribution layer around the embossing points in this layer, which promotes the introduction of fluid into the storage layer lying thereunder.

BRIEF DESCRIPTION OF THE DRAWING

Additional features, details and advantages of the invention are found in the appended patent claims and in the drawings and subsequent description of one aspect of the invention.

DETAILED DESCRIPTION

Figure 1:
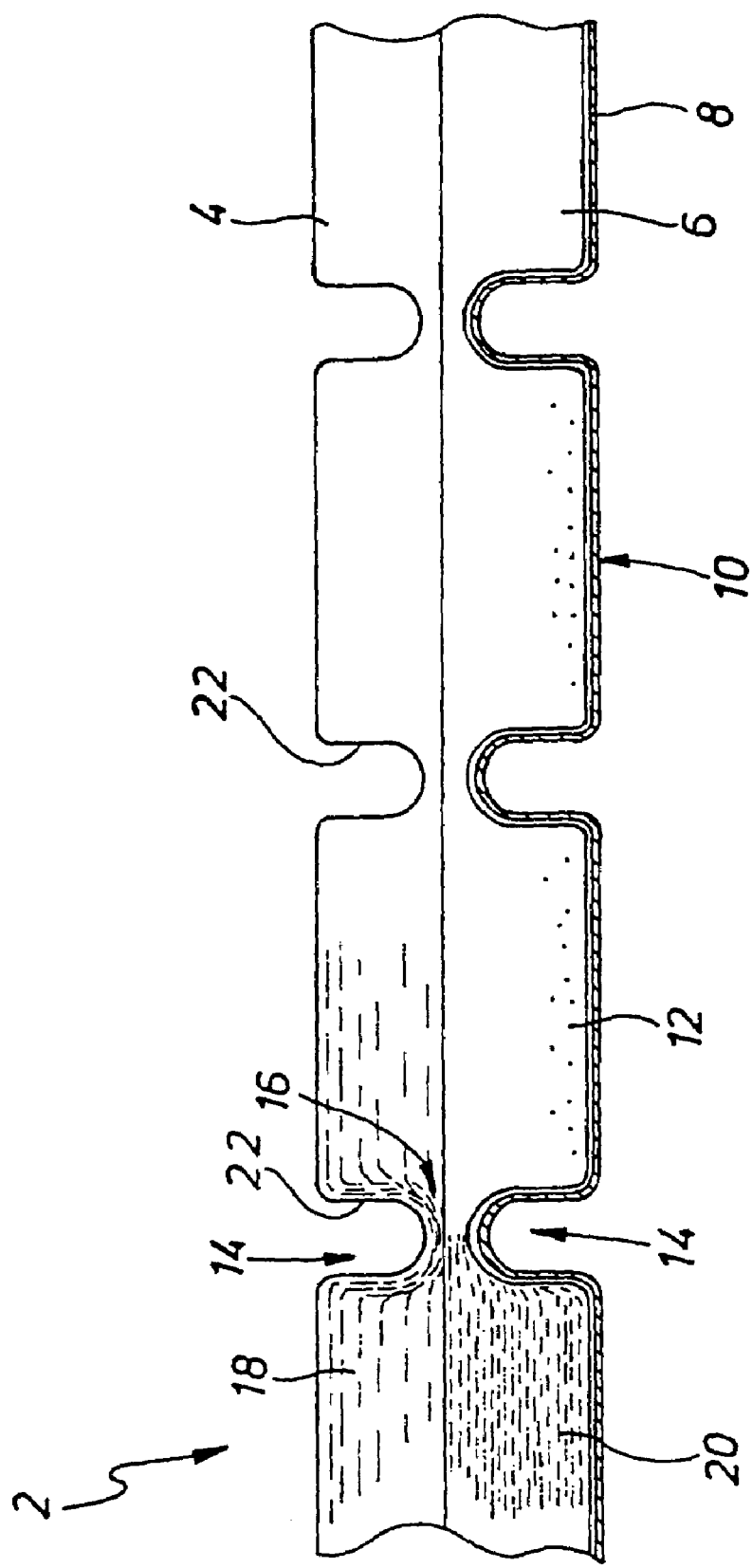
FIG. 1 is a cross-sectional view of an absorbent body in accordance with the invention for a sanitary napkin.

With the invention, it was established that by joining the at least two layers through a punctiform embossed pattern in the large-pored fluid absorption and distribution layer, outstanding fluid management properties can be achieved. Through the punctiform embossing of the layers, a large-pore inter-fiber space is retained in the area between the embossing points, i.e., a large fluid absorption volume. As a result of the embossing points, an essentially funnel-shaped pore gradient is formed around them, i.e., increasing density with an accompanying corresponding decrease in pore size in a funnel-shaped area around the particular embossing point toward the center of the embossing. The center acts as a suction or drainage point within the large-pored fluid absorption layer and results in selective drainage and fluid introduction at these points into the storage layer lying thereunder. A funnel-shaped pore gradient and a funnel-shaped area described above is intended to convey that this area surrounds a particular embossing point; it does not have to be strictly funnel or cone-shaped, but it follows the geometry of the embossing site directed at the specific embossing point, which is still oriented to its center in the manner of a funnel.

The grid-like disposition of the embossing points not only results in the bonding of the at least two layers to produce a preferably adhesive-free composite layer, but the fluid absorption and transportation function of the fluid absorption layer facing the body is hereby improved.

The base weight of the composite layer is preferably 200-500 g/m$^2$, specifically 300-400 g/m$^2$. The weight ratio by percent of the fluid absorption and distribution layer facing the body to the total mass preferably amounts to 10-45%, specifically 25-30%.

The area of the embossing points preferably measures 0.25 to 4 mm$^2$. The ratio of the area of the embossing points to the total area of the fluid absorbing layer viewed in projection preferably measures 2 to 35, specifically 5 to 15%.

As with the production of the embossing points in accordance with EP 1 032 342 B1, the embossing points can be furnished from both sides and align with each other exactly.

In a further aspect of the composite layer, the embossing is also applied through a top sheet preferably provided on the side of the absorbent layer facing away from the body. If this top sheet is advantageously formed by a tissue layer, a surface configuration providing grip is created which is easily handled during production and which protects the storage layer from "unraveling."

A hygiene article is the further subject of the invention, specifically a women's sanitary napkin or panty liner, which is characterized by an absorbent body of the previously described type in accordance with the invention.

FIG. 1 shows an absorbent body for a hygiene article, for example, a sanitary napkin or panty liner, identified overall by reference number 2. The absorbent body 2 has an upper fluid absorption and distribution layer 4 facing the body and a fluid storage layer 6 disposed thereunder facing away from the body and a tissue top sheet 8 on the side of the storage layer 6 facing away from the body.

The fluid absorption and distribution layer 4 preferably consists of 100% of intralinked cellulose fibers, and the fluid storage layer 6 preferably consists from 20 to 90% by weight of natural cellulose fibers (cellulose). The fluid storage layer 6 can also comprise super absorbent polymer materials, hydrogel-forming materials, and other additives as needed. Preferably the storage layer 6 is formed of natural cellulose fibers and super absorbent materials.

On the side of the storage layer 6 facing away from the body, a thin, tissue layer of cellulose fibers is provided which conforms to the storage layer and constitutes an easy-to-grip, relatively smooth surface 10, which prevents the storage layer 6 from unraveling. In addition, this tissue layer 8 prevents particulate, super absorbent materials 12 from escaping from the storage layer.

During the manufacture of the composite layer, a mixture of cellulose fibers and super absorbent particles is first deposited using the air laying process on a tissue layer being transported in the direction of the web and then basically pre-compressed to the capillary pore volume required for a storage layer between the cellulose fibers to create the storage layer 6.

After that, intralinked cellulose fibers are deposited to form the fluid absorption and distribution layer. The loose fiber layering thus formed is brought to a pair of calendaring rollers with nubs forming embossing means in accordance with EP 1 032 342 B1. The nubs are distributed over the surface of the calendaring rollers according to a regular grid pattern. They have an embossing surface area of 0.2 to 4 mm$^2$.

The arrangement of the calendaring rollers and the pattern of the embossing nubs to each other and the determination of the calendar roller gap is preferably such that the embossing surfaces of the nubs almost touch. Depending on the thickness of the pre-compressed fiber layering and the mass of the fibrous material, a gap is selected between the embossing surfaces of the nubs such that a grid-like embossing of the layers is created which does not become detached when used properly, when the laminate is handled and also in a hygiene article.

FIG. 1 shows the previously described calendared composite layer viewed in cross section. Embossing locations 14 can be seen, which extend from both sides of the absorbent body 2 essentially perpendicular to the plane of the web into the absorbent body material. A highly compressed area 16 remains, which is not shown to scale in the drawing, in which the fibers of the layers 4, 6 and also 8 are pressed insolubly together and thus form an inseparable composite layer.

As indicated on the left of FIG. 1, the pore volume, that is, the space 18 between the fibers forming layer 4, is much larger than that 20 of the distribution layer and so it consequently has very high capillarity. The capillarity constitutes part of its ability to transport fluid from the point of impingement to unused areas of the storage layer 6.

It has been established that producing embossing points 14 in the fluid absorption area 4 in a grid pattern results advantageously in the creation of funnel-shaped pore gradients in the fluid absorption layer 4. A plurality of local drainage sites within the fluid absorption layer is thereby created, which, incidentally, has a greater pore volume than the storage layer disposed thereunder. There is no deviation from the concept of the large-pore fluid absorption layer, wherein drainage sites are created selectively and in a grid pattern through the punctiform embossing of the layers. These sites, as shown, promote the introduction of fluid into the storage layer located thereunder. Furthermore, the embossing points 14 represent additional volume 22 for the initial absorption of impacting fluid.

The absorbent body 2 described above can be used as an absorbent body in a hygiene article in which a preferably fluid-impermeable film layer is furnished on the side facing away from the body and, on the side facing the body, a fluid-permeable nonwoven cover could be furnished as top sheet material. If necessary, one or more additional large-pore materials, preferably nonwoven materials, specifically polyester based, can be disposed between the top sheet and the absorbent body to act as distribution layers.

What is claimed is:

1. An absorbent body for hygiene articles comprising: a fluid absorption and distribution layer facing a body, the fluid absorption and distribution layer made of a first fibrous material with a first pore size composed of air laid intralinked highly porous lofty cellulosic fibers; a fluid storage layer facing away from the body, the fluid storage layer containing at least 20-98% by weight of cellulose fibers, the fluid storage layer having a second pore size, which is smaller than the first pore size; and wherein the absorption and distribution layer and the fluid storage layer are bonded together by a plurality of adhesive-free embossing points arranged in a grid pattern forming a composite layer; and wherein a pore gradient is formed around each adhesive-free embossing point in the fluid absorption and distribution layer, wherein the pore gradient is configured to promote introduction of fluid into the storage layer disposed thereunder, and wherein the embossing points are furnished from both sides of the composite layer and corresponding embossing points from opposing sides align with each other.

2. The absorbent body in accordance with claim 1, wherein the base weight of a composite layer formed of the fluid absorption and distribution layer and the fluid storage layer bonded together measures 200-500 g/m$^2$.

3. The absorbent body in accordance with claim 1, wherein the weight by percent of the fluid absorption and distribution layer measures 300-400 grams/m$^2$.

4. The absorbent body in accordance with claim 1, wherein the embossing points comprise a surface area between 0.25 to 0.4 mm$^2$.

5. An absorbent body for hygiene articles comprising: a fluid absorption and distribution layer facing a body, the fluid absorption and distribution layer made of a first fibrous material with a first pore size composed of air laid intralinked highly porous lofty cellulosic fibers; a fluid storage layer facing away from the body, the fluid storage layer containing at least 20-98% by weight of cellulose fibers, the fluid storage layer having a second pore size, which is smaller than the first pore size; and wherein the absorption and distribution layer and the fluid storage layer are bonded together by a plurality of adhesive-free embossing points arranged in a grid pattern forming a composite layer; and wherein a pore gradient is formed around each adhesive-free embossing point in the fluid absorption and distribution layer, wherein the pore gradient is configured to promote introduction of fluid into the storage layer disposed thereunder, and wherein the embossing points are provided from both sides of a composite layer formed of the bonded fluid absorption and distribution layer and the fluid storage layer and corresponding embossing points from opposing sides are aligned with each other.

6. The absorbent body in accordance with claim 1 further comprising a top sheet furnished on a side of the fluid storage layer facing away from the body, the top sheet having embossing points corresponding to the adhesive-free embossing points.

7. The absorbent body in accordance with claim 6, wherein the top sheet is a tissue sheet.

8. A hygiene article, characterized by an absorbent body in accordance with claim 1.

9. The absorbent body in accordance with claim 1, wherein the base weight of a composite layer formed of the fluid absorption and distribution layer and the fluid storage layer bonded together measures 300-400 g/m².

10. The absorbent body in accordance with claim 1 wherein the pore gradient formed around each adhesive free embossing point is funnel shaped.

* * * * *